United States Patent

Kappelt et al.

[11] Patent Number: 5,819,685
[45] Date of Patent: Oct. 13, 1998

[54] TRAY FOR RAISING INSECT LARVA

[75] Inventors: Charles E. Kappelt, Linesville; Thomas E. Levenhagen, Meadville, both of Pa.

[73] Assignee: Molded Fiber Glass Companies, Linesville, Pa.

[21] Appl. No.: 821,962

[22] Filed: Feb. 19, 1997

Related U.S. Application Data

[60] Provisional application No. 60/029,434 Nov. 12, 1996.

[51] Int. Cl.[6] .................................................. A01K 67/033
[52] U.S. Cl. ........................ 119/6.5; 119/322; 119/6.6; 206/503
[58] Field of Search ............................. 119/6.5, 6.6, 322; 206/503, 510; 426/3; 47/1.1, 1.4

[56] References Cited

U.S. PATENT DOCUMENTS

| | | |
|---|---|---|
| 2,255,036 | 9/1941 | Gedge ....................................... 119/322 |
| 2,670,562 | 3/1954 | Gould ........................................ 119/6.5 |
| 3,106,332 | 10/1963 | Dieguez ................................... 206/510 |
| 3,750,625 | 8/1973 | Edwards ................................... 119/6.5 |
| 4,227,642 | 10/1980 | Ortel ....................................... 206/510 |
| 4,487,317 | 12/1984 | Sanderson ............................... 206/509 |
| 4,671,411 | 6/1987 | Rehrig et al. ........................... 206/510 |
| 5,179,913 | 1/1993 | Cannon ................................... 119/322 |
| 5,351,643 | 10/1994 | Hughes ................................... 119/6.5 |

OTHER PUBLICATIONS

Molded Fiber Glass Tray Company Part No. 805–208 (2 pages).

*Primary Examiner*—John J. Wilson
*Attorney, Agent, or Firm*—Lovercheck and Lovercheck

[57] ABSTRACT

A tray suitable for use in mass raising insect larva, particularly flys (flies), in and artificial environment from incubation through hatching and growth and including a smooth bottom and four upwardly extending sides being open about fifty percent (50%) of the total height to provide sufficient ventilation to maintain a predetermined temperature to satisfy the developing process. The trays are stackable and have ribs at their corners to provide structural strength.

8 Claims, 3 Drawing Sheets

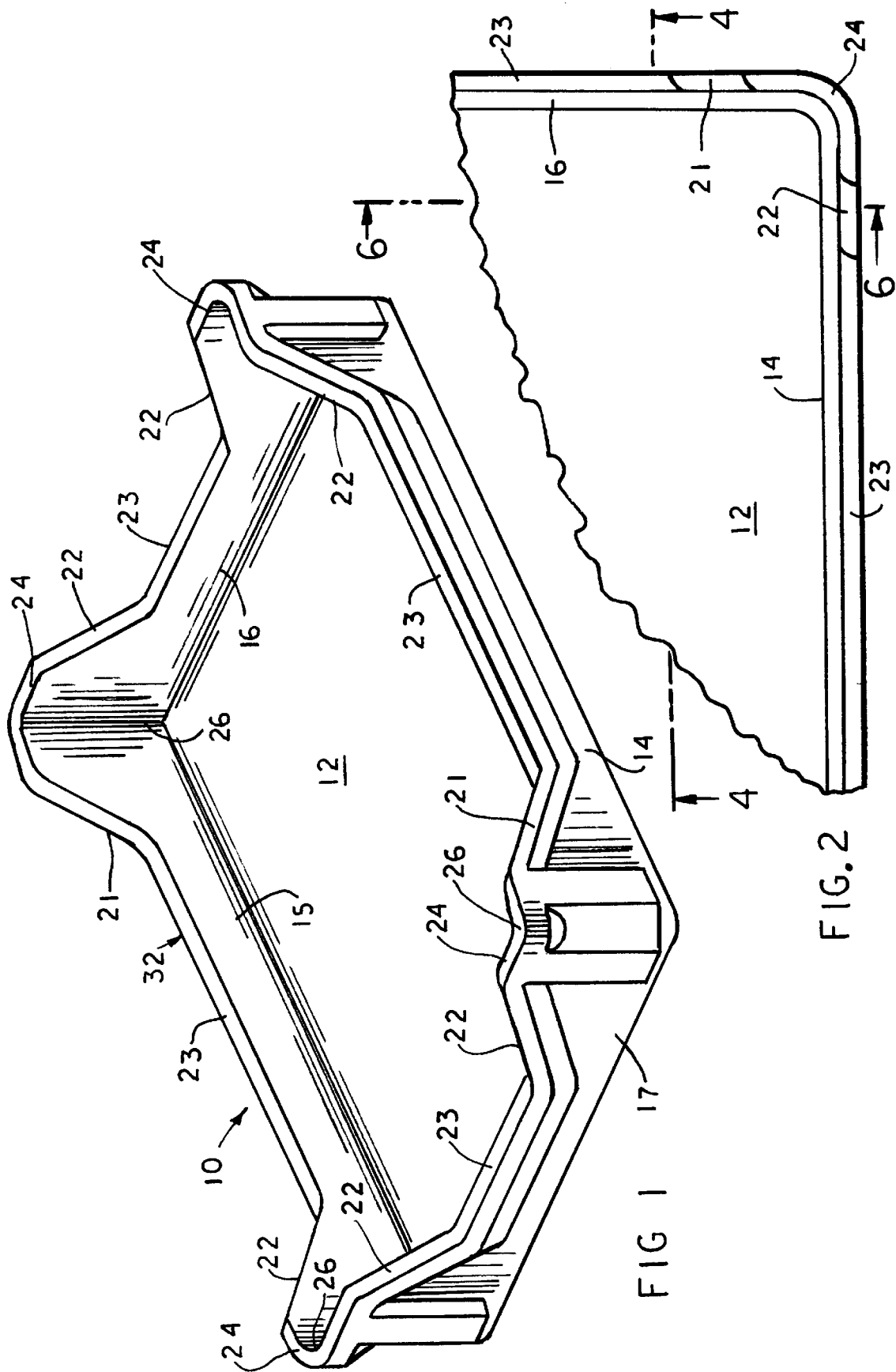

TRAY FOR RAISING INSECT LARVA

BACKGROUND OF THE INVENTION

This application claims the benefit of U.S. Provisional Application Ser. No. 60/029,434 filed Nov. 12, 1996.

Some of the problems of insect rearing are explained in U.S. Pat. No. 3,750,625.

SUMMARY OF THE INVENTION

A tray suitable for raising insect larva is made from reinforced thermoset composite material. The design has four sides dropped more than fifty percent of the total height. This provides sufficient ventilation to maintain a specified temperature for air circulation thus to satisfy the developing process of the larva. The structure of the trays provides for stacking, ventilation control and strength for heavy loads of stacked trays. The smooth surface and designed radii provide for ease of cleaning required in a sanitary operation.

The reinforced thermoset composite material used in the tray construction is resistant to attack from cleaning solutions and disinfectants. There are no seams or sharp corners to trap material placed in the tray. The dimensions are constant which allows for correct ventilation and load bearing characteristics.

It is an object of the present invention to provide a tray for stacking, ventilation control and strength for heavy loads.

It is an object of the invention to provide an improved insect larva tray.

Another object of the invention is to provide an insect larva tray that can be stacked in other trays.

Another object of the invention is to provide an insect tray that provides ventilation to maintain a specified temperature for air circulation between the sides of the stacked trays.

It is another object of the present invention to provide a tray that is simple in construction, economical to manufacture and simple and efficient to use.

With the above and other objects in view, the present invention consists of the combination and arrangement of parts hereinafter more fully described, illustrated in the accompanying drawing and more particularly pointed out in the appended claims, it being understood that changes may be made in the form, size, proportions and minor details of construction without departing from the spirit or sacrificing any of the advantages of the invention.

BRIEF DESCRIPTION OF THE DRAWING(S)

FIG. 1 is a perspective view of the tray for raising insect larva showing the four open sides for ventilation.

FIG. 2 is a fragmentary plan view of the tray for raising insect larva.

DESCRIPTION OF THE PREFERRED EMBODIMENT(S)

Figure 3:
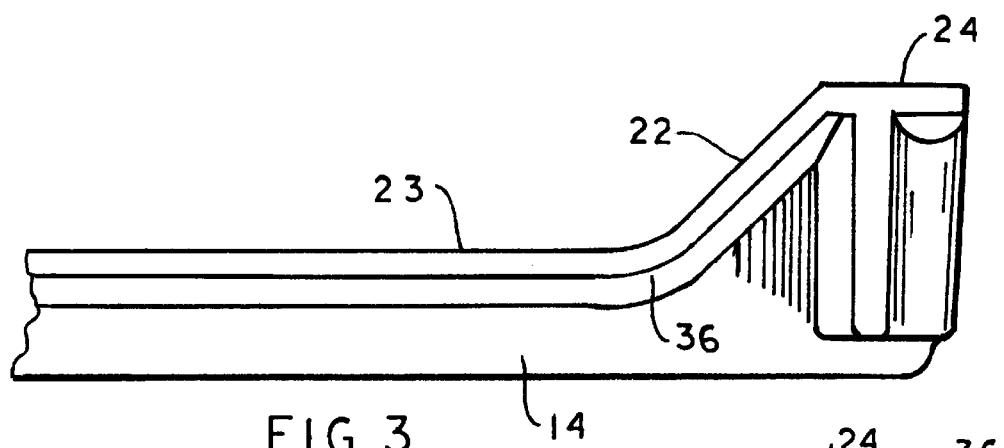
FIG. 3 is a fragmentary side view of the tray.
Figure 4:
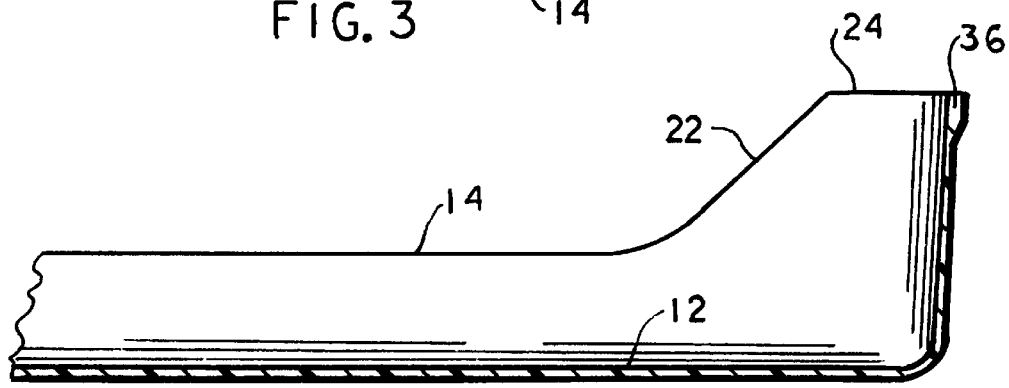
FIG. 4 is a fragmentary sectional side view taken along line 4—4 of FIG. 2.
Figure 5:
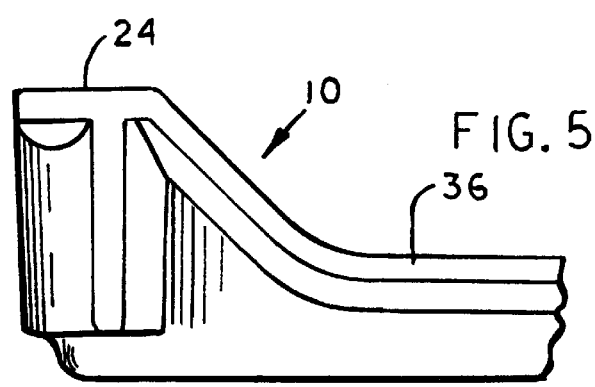
FIG. 5 is a fragmentary end view of the tray.
Figure 7:
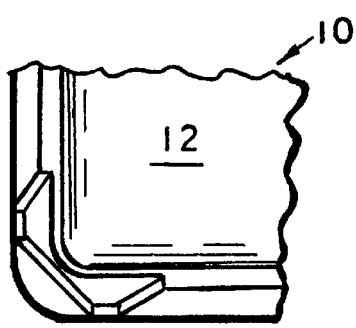
FIG. 7 is a fragmentary bottom view of a corner of the tray showing the interlocking stacking structure of the tray.
Figure 6:
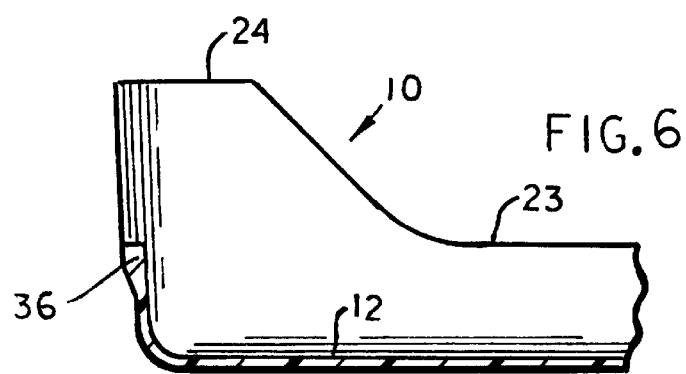
FIG. 6 is a fragmentary sectional side view taken along line 6—6 of FIG. 2.
Figure 8:
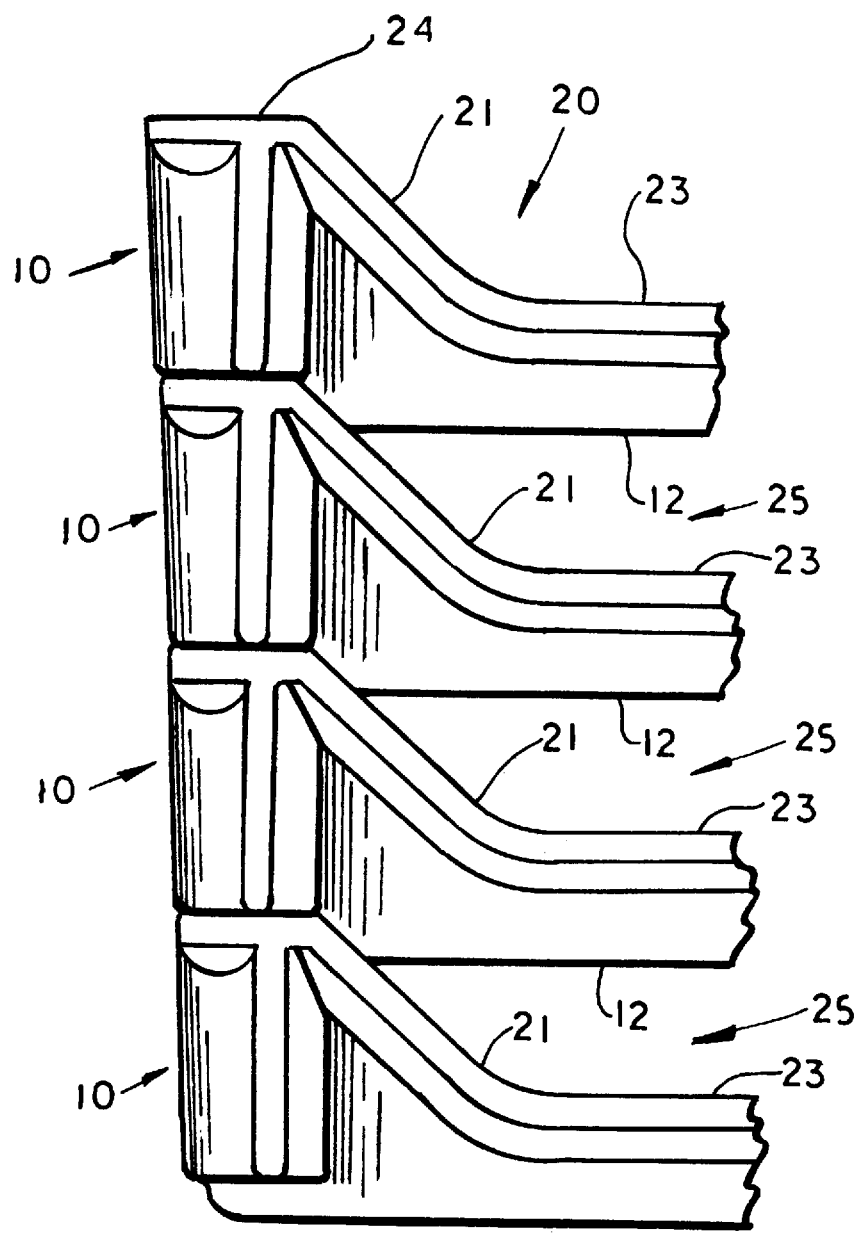
FIG. 8 is a fragmentary end view of several trays in interlocking stacked position as the trays would be used to raise insect larva.

Now with more particular reference to the drawings, FIGS. 1 through 8 show tray 10 for insect rearing made up of bottom 12, first side 14, second side 15, first end 16 and second end 17, all integrally attached together.

Sides 14,15 are integrally attached to ends 16,17 thereby forming four corners 26. Each side 14,15 and lock ends 16,17 has flat intermediate flat top edge and arcuate corner part 30. Each corner 26 has generally flat top side surface 24 and second inclined portion 22 extending upwardly to flat upper portion 24. Second inclined portion 22 extends upwardly at about 30 degrees. Thickened bead 32 extends entirely around the top surface of the side parts, end parts and the corner parts providing reinforcement to sides 14,15, ends 16,17 and corners 26 and distribute concentrated forces that may compose on sides 14,15 and ends 16,17. Flat top surfaces 24 of corner parts 26 that are disposed in a first plane above a second plane of flat side surfaces 23 providing ventilation space 25 above side surfaces 28. The next tray 10 is stacked on top of this tray 10 at a distance from bottom 12 about half the distance from top surface 24 to the bottom of the tray above. Spaced ribs 32 are integrally attached to corner parts 26 and to thickened ribs 32. Ribs 32 provide structural strength for supported stacked trays.

The foregoing specification sets forth the invention in its preferred, practical forms but the structure shown is capable of modification within a range of equivalents without departing from the invention which is to be understood is broadly novel as is commensurate with the appended claims.

The embodiments of the invention in which an exclusive property or privilege is claimed are defined as follows:

1. A tray for rearing insects comprising sides, ends and a bottom all connected together forming an open top container having four corner parts;

each said side having an intermediate part and a corner part;

said intermediate part of each said side having a top edge generally parallel to said bottom;

each said corner part of each said side extending upwardly and toward said corner from said intermediate part at an acute angle to a generally flat surface;

said flat top and said corner surfaces of said sides provides a supporting surface for the bottom of another tray to be disposed generally parallel to said top edge of said intermediate parts of said sides thereby providing a first ventilation space for insects in said tray;

said ventilation spaces having a height equal to about half the total height of said flat top of said corner above said tray bottom.

2. The tray recited in claim 1 wherein each said end has an intermediate part;

said intermediate part of each said end having a top edge generally parallel to said top edge of said intermediate part and said sides and the top edges of said ends extend upwardly from said top edge to said top edge of said corner part at an acute angle to said bottom thereby providing a second ventilation space having a height about equal to said height of said first ventilation space.

3. The tray recited in claim 1 wherein said acute angle is about thirty degrees.

4. The tray recited in claim 1 wherein said corner part terminates at a bead substantially thicker than said corner part;

rib means attached to said corner parts and extending from said bottom to said top edge providing load bearing structural strength for stacked trays.

5. The tray recited in claim 4 wherein said bead extends around said top edge and said sides and along said top edges of said ends forming a continuous bead around the top of said tray.

6. The tray recited in claim 1 wherein a thickened bead having a thickness substantially greater than said side ends and said corners is attached to said side of said ends and said corners and extends continually around said sides, said ends and said corners;

at least one rib is attached to each said corner on the outer side thereof;

said rib extends from said bottom to said thickened bead and provides structural strength to support other trays stacked on said tray.

7. The tray recited in claim 6 wherein two said ribs are attached to each said corner;

each of said two ribs are spaced from each other.

8. The tray recited in claim 7 wherein said tray is adapted to be stacked on said flat surfaces;

said ribs of said trays being disposed in vertical alignment with each other whereby said ribs of each said tray carries the weight of said trays above.

* * * * *